(12) United States Patent
Kidouchim (10) Patent No.: US 7,229,168 B2
(45) Date of Patent: *Jun. 12, 2007

(54) MULTI-FACETED MAGNETIC HINGE SYSTEM FOR COUPLING OBJECTS, INCLUDING EYEWEAR

(76) Inventor: Armand Kidouchim, 24735 Avenida Asoleada, Calabasas, CA (US) 91302-1412

( * ) Notice: Subject to any disclaimer, the term of this patent is extended or adjusted under 35 U.S.C. 154(b) by 205 days.

This patent is subject to a terminal disclaimer.

(21) Appl. No.: 11/114,471

(22) Filed: Apr. 25, 2005

(65) Prior Publication Data

US 2005/0200802 A1    Sep. 15, 2005

Related U.S. Application Data

(63) Continuation-in-part of application No. 10/836,748, filed on Apr. 29, 2004, now Pat. No. 6,939,003, which is a continuation-in-part of application No. 10/659,227, filed on Sep. 9, 2003, now Pat. No. 6,869,180, and a continuation-in-part of application No. 10/644,631, filed on Aug. 19, 2003, now abandoned.

(60) Provisional application No. 60/567,335, filed on Apr. 30, 2004.

(51) Int. Cl.
 *G02C 9/00* (2006.01)
(52) U.S. Cl. .............................. 351/47; 351/57; 16/228
(58) Field of Classification Search ................. 351/47, 351/57, 48, 44, 41, 155, 158; 16/228
See application file for complete search history.

(56) References Cited

U.S. PATENT DOCUMENTS

| | | |
|---|---|---|
| 5,335,025 A | 8/1994 | Wang |
| 5,568,207 A | 10/1996 | Chao |
| 5,737,054 A | 4/1998 | Chao |
| 5,786,880 A | 7/1998 | Chao |
| 5,883,688 A | 3/1999 | Chao |
| 6,012,811 A | 1/2000 | Chao et al. |
| 6,089,708 A | 7/2000 | Ku |
| 6,092,896 A | 7/2000 | Chao et al. |
| 6,109,747 A | 8/2000 | Chao |
| 6,352,342 B1 | 3/2002 | Huang |
| 6,354,703 B1 | 3/2002 | Sadler |
| 6,488,372 B1 | 12/2002 | Park |
| 6,533,411 B1 | 3/2003 | Chen et al. |
| 6,595,635 B2 * | 7/2003 | Schubert ..................... 351/155 |
| 6,939,003 B2 * | 9/2005 | Kidouchim .................. 351/47 |
| 2002/0140897 A1 | 10/2002 | Huang |
| 2003/0112408 A1 | 6/2003 | Zeiman |

* cited by examiner

*Primary Examiner*—Hung Xuan Dang
(74) *Attorney, Agent, or Firm*—Kelly Lowry & Kelley LLP (57) ABSTRACT

A magnetic hinge system includes a first hinge member associated with a first object, such as the frame of a primary eyewear, and having outwardly-facing facets. A second hinge member is attached to second object, such as a secondary eyewear, and defines a slot having inwardly-facing facets configured to overlie less than all of the outwardly facing facets of the first hinge member. At least some of the facets are magnetized or include magnets to couple the second hinge member to the first hinge member, and permit selective segmented rotation relative to one another. The second hinge member may also define a second slot configured for insertion of a portion of the secondary eyewear therein. A track may be used for supporting at least one hinge member, and provide attachment to a bill of a visor or hat.

27 Claims, 9 Drawing Sheets

MULTI-FACETED MAGNETIC HINGE SYSTEM FOR COUPLING OBJECTS, INCLUDING EYEWEAR

RELATED APPLICATION

This application claims priority to U.S. Provisional Application No. 60/567,335, filed 30 Apr. 2004; and is a continuation-in-part application of U.S. patent application Ser. No. 10/836,748, filed 29 Apr. 2004 now U.S. Pat. No. 6,939,003, which is a continuation-in-part application of U.S. patent application Ser. No. 10/659,227, filed 9 Sep. 2003 and issued as U.S. Pat. No. 6,869,180; and is also a continuation-in-part application of U.S. patent application Ser. No. 10/644,631, filed 19 Aug. 2003 now abandoned.

BACKGROUND OF THE INVENTION

The present invention generally relates to hinge systems. More particularly, the present invention resides in a magnetic hinge system for detachably coupling safety eyewear to a primary eyewear, visor or the like.

People often wear eyeglasses to correct their vision, be it near-sighted or far-sighted. The eyeglasses have a main frame with lenses fitted thereto. Protective-lens eyeglasses are also available of generally the same construction.

There are instances, such as when in the sun, when an auxiliary eyewear, such as sunglasses, is desirable. There exist clip-on sun shades which are clipped to the rim or frame of the primary eyeglasses. However, most such sun shades are typically not able to be pivoted upwardly and out of view, such as when entering a building or the like from outdoors. Instead, the sun shades must be completely removed and stored in a pocket or the like of the eyeglass wearer.

Advancements in the field have led to the use of magnetic members which are used to removably attach the sun shade or auxiliary lenses to the eyeglasses. However, the magnetic connections are typically not pivotally arranged so as to enable the user to "flip-up" the sun shades away from the eyeglass lenses.

Yet other prior art auxiliary eyewear require specially manufactured eyeglasses for a stable connection. Alternatively, the auxiliary eye shades must be semi-permanently attached to the eyeglasses, such as using screws or the like. Of course, this does not enable the eyeglass wearer to conveniently remove the sun shades or auxiliary lenses.

In addition to the shortcomings described above, prior art auxiliary eyewear in general has the shortcoming that they are not adapted to be connected to any piece of eyewear. That is, the prior art auxiliary eyewear does not have universal connection means. Instead, they rely upon clips or attachments to the eyeglass to the primary eyeglasses which are usually very specific in nature. If not completely specific, the auxiliary eyewear still suffers a drawback of connecting to the primary eyewear in such a manner so as to limit it to only several styles of eyewear. This is due to the differences between the "nose bridge" portion of the frames and the size of the frames of the primary eyewear which varies dramatically between different styles.

There are many instances when safety eyewear is necessary. For example, in certain industries such as machining, tooling, woodworking, etc. safety eyewear is necessary to prevent the occasional projectile from entering into the worker's eyes.

In these instances, safety eyeglasses, goggles, or face masks are often used. Face masks are often used when foreign material is kept away from the entire face of the user or operator, such as a surgeon or the like, as well as the eyes. Oftentimes, however, these safety eyewear or masks are not comfortable to the user or are limited in their adjustability. This is particularly the case when the operator of the machine, surgeon, etc. wears prescription eyewear or must wear of utilize magnifying lenses to perform their duties. In this case, safety eyeglasses are typically not equipped to be placed over the prescription eyeglasses. Although goggles can be placed over the prescription eyewear, this is often uncomfortable.

There is a desire to have the safety shield or glasses selectively pivotally moved in front of the face, when protection if necessary, and away from the face or eyes for better vision when the danger of body fluids, projectiles, etc. is must present. Of course, the safety eyewear should be connected to the primary eyewear wearer, or otherwise positioned in front of the eyes and face of the user, so as not to become dislodged when hit by a projectile or the like.

Accordingly, there is a continuing need for a system for detachably connecting a safety shield or eyewear over a user's face, particularly over a primary eyewear, such as prescription eyeglasses. Such safety eyewear should preferably be able to be pivoted out of the field of view of the user when desired. However, the attachment system should also be capable of withstanding a sufficient force by flying projectiles without becoming dislodged from the primary eyewear, cap, or head of the operator. The present invention fulfills these needs and provides other related advantages.

SUMMARY OF THE INVENTION

The present invention relates to a multi-faceted magnetic hinge system. The magnetic hinge system of the present invention is designed to rotatably and removably couple objects. A first hinge member attached to a first object defines a hinge access having a plurality of generally planar outwardly-facing facets. A second hinge member is attached to the second object, and defines a slot having a plurality of generally planar inwardly-facing facets configured to overlie less than all of the outwardly-facing facets. At least some of the facets are magnetized or include magnets, to couple the first and second hinge members to one another and permit selected segmented rotation relative to one another.

In particular, the magnetic hinge system is adapted to rotatably and removably couple primary and secondary eyewear. In particularly preferred embodiments, at least one of the primary or secondary eyewear comprises safety eyewear which shields and protects the user's eyes or face from body fluids, dangerous projectiles, etc.

In one embodiment, a first hinge member is associated with the frame of the primary eyewear. Typically, a cross-bar is attached to the primary eyewear frame and supports the first hinge member. The cross-bar may be attached at opposite ends thereof to a plate which is attached to the primary eye frame between a pair of lenses thereof. The first hinge member defines a hinge axis, and has a plurality of generally planar outwardly-facing facets disposed about the hinge axis.

A second hinge member is attached to the secondary eyewear and defines a slot having a plurality of generally planar inwardly-facing facets configured to overlie less than all of the outwardly-facing facets. At least some of the facets of the second hinge member are magnetized or include magnets, to couple the second hinge member to the first hinge member and permit selective segmented rotation of the second hinge member relative to the first hinge member about the hinge axis.

Preferably, the first hinge member includes at least five facets. The second hinge member includes at least half as many facets as the first hinge member, so that approximately 180° of the exterior surface of the first hinge member is overlaid by the second hinge member. In a particularly preferred embodiment, the first hinge member comprises a hexagon, and a second hinge member includes three facets overlying three outwardly-facing facets of the hexagon simultaneously. Typically, the facets of the second hinge member engage rear facets of the first hinge member when a primary and secondary eyewear are positioned parallel to one another.

Typically, the second hinge member defines a second slot which is configured for insertion of a portion of the secondary eyewear therein. The second slot may include a fastener for retaining the secondary eyewear therein.

In another embodiment, the magnetic hinge system comprises a track which is adapted for attachment to a first object, such as a bill of a hat or visor. The track has a first hinge member associated therewith.

A second hinge member is attached to a second object, such as auxiliary eyewear comprising a safety shield or eyewear. Once again, the second hinge member may include a slot configured for insertion of a portion of the auxiliary eyewear therein and a fastener for retaining the secondary eyewear.

Primary eyewear may extend downwardly from the tracks in front of the eyes of the user. In such a case, a third hinge member is attached to the track and defines a hinge axis. The third hinge member, similar to the first hinge member, has a plurality of generally planar outwardly-facing facets disposed about the hinge axis. A fourth hinge member, similar to the second hinge member, is attached to the primary eyewear and has a plurality of generally planar inwardly-facing facets configuring to overlie less than all of the outwardly-facing facets of the first hinge member or of the third hinge member. At least some of the facets of the hinge members are magnetized or include magnets to couple the third and fourth hinge members and permit selective segmented rotation relative to one another.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings, for purposes of illustration, the present invention is directed to a magnetic hinge system for rotatably and removably coupling objects, such as eyewear. In particular, the system of the present invention detachably connects a safety shield or eyewear over a user's face, or over a primary eyewear, such as prescription glasses. The system is designed such so as to enable the safety eyewear to be pivoted out of the field of view of the user, yet also capable of withstanding a force by flying projectiles without becoming dislodged from the primary eyewear or head of the user.

Although the invention is described herein as it relates to coupling eyewear, such as a safety shield and primary eyewear, it will be appreciated by those skilled in the art that the magnetic hinge system of the present invention can be used with a variety of other objects. For example, the magnetic hinge system can be used for coupling a door to a door frame, a window to a window sill, or any other two objects which are pivotally and rotatably coupled to one another. Thus, although the invention is particularly adapted for coupling eyewear, it is not limited to such.

Figure 1:
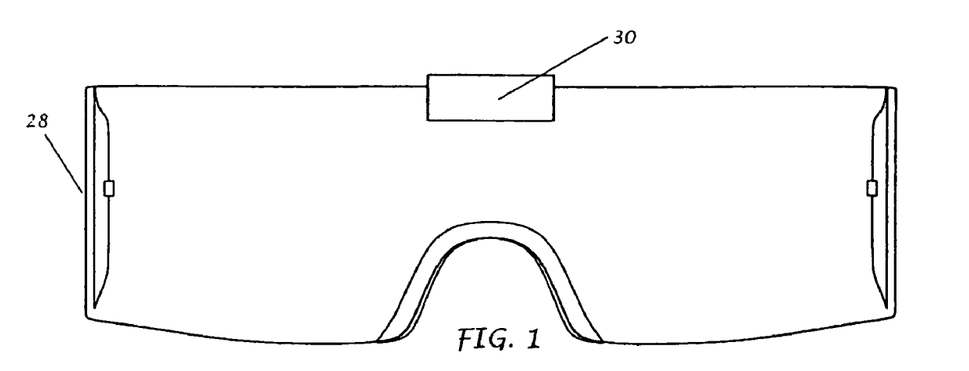
FIG. 1 is a front elevational view of a safety auxiliary wear, used in accordance with the present invention.
Figure 2:
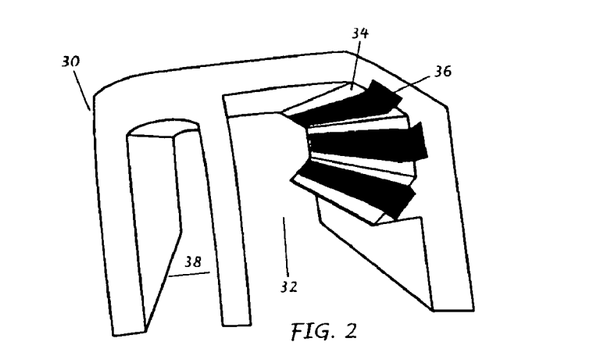
FIG. 2 is a side perspective view of a hinge member operably coupled to the safety eyewear of FIG. 1.
Figure 3:
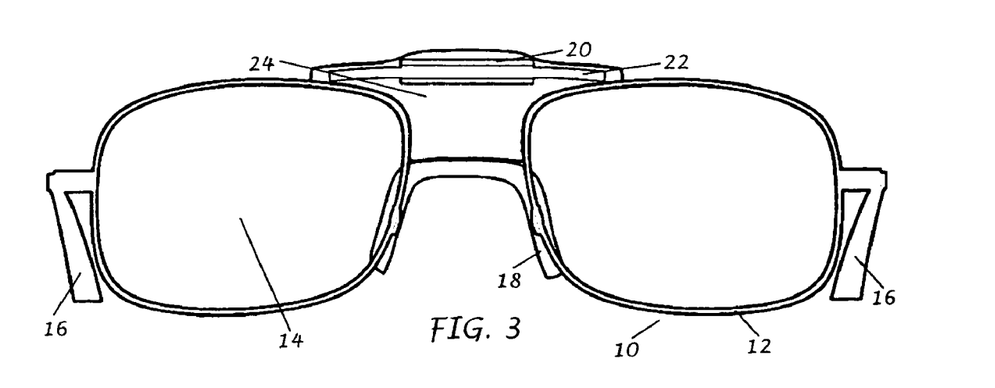
FIG. 3 is a front elevational view of primary eyewear, modified in accordance with the present invention.

With reference now to FIGS. 1–4, in one embodiment of the invention, primary eyewear 10, such as prescription eyeglasses, are modified, as illustrated in FIG. 3. It is commonly known that such eyewear includes a frame 12 surrounding and retaining a pair of lenses 14, which may be prescription lenses. Typical eyeglasses 10 also include extensions 16 for securing the eyeglasses 10 between the head and ears of the user. The eyeglasses 10 may also include nose pads 18 or the like, for comfortably resting the glasses 10 on the bridge of one's nose.

The eyeglasses 10 are modified in accordance with the present invention by securing a first hinge member 20 to the eyeglasses 10, such as by a cross-bar 22 extending from the first hinge member 20 to the frame 12 of the eyeglasses 10. Typically, however, due to the fact that safety eyewear are intended to be coupled with the primary eyewear 10, a bar or plate 24 is typically bonded to the frame 12 of the primary eyewear 10, such as with adhesive, soldering, or the like, and the cross-bar 22 connected to the plate 24. In this manner, if the hinge member 20 receives a force, such as from a projectile, the plate 24 will be better able to absorb this force without breaking.

Figure 4:
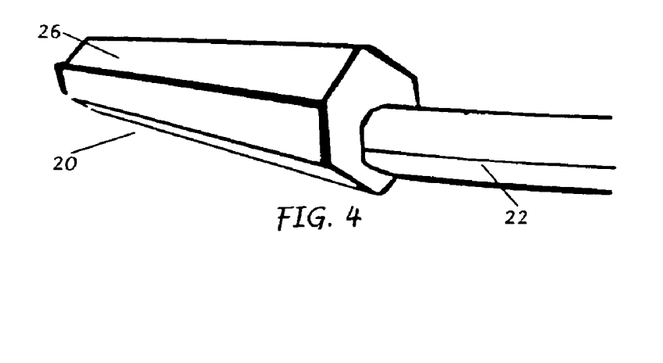
FIG. 4 is an enlarged view of a hinged member attached to the primary eyewear of FIG. 3.

With reference now to FIG. 4, the primary hinge member 20 includes a plurality of facets 26. Preferably, the facets 26 extend substantially around the entire exterior surface of the hinge member 20. Typically, the hinge member 20 includes at least five facets, and more preferably comprises a hexagon having six facets, as illustrated. These planar outwardly-facing facets 26, in a preferred embodiment, are angled from one another by approximately 60°.

With reference now to FIGS. 1 and 2, as described above, the invention includes a secondary eyewear 28, which is typically in the form of safety eyewear, such as the illustrated safety goggles of FIG. 1, a safety face shield, etc. A second hinge member 30, is attached to the secondary or auxiliary eyewear 28. More particularly, with reference to FIG. 2, the second hinge member 30 defines a first slot 32 having a plurality of inwardly-facing facets 34.

Preferably, at least the second hinge member 30 includes at least half as many facets 34 as the first hinge member 20 has external facets 26. In the illustrated embodiment, there are three inwardly-directed facets 34 for engagement with three of the facets 26 of the first hinge member 20. The facets 34 are magnetized, or more typically include magnets 36 embedded therein or adhered thereto, for coupling to the metallic hinge member 20. The first hinge member 20 may include magnets having an opposite polarity facing outward, but more typically the hinge member 20 is comprised of a metal material containing iron or the like so as to be attracted to the magnets 36. It will be appreciated that the facets 34 and 26 compliment one another so as to be mated and magnetically coupled to one another.

Figure 5:
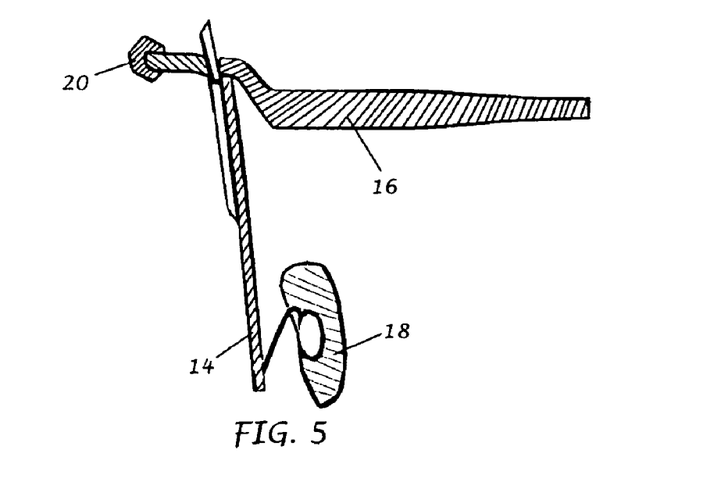
FIG. 5 is a cross-sectional view of the primary eyewear of FIG. 3.
Figure 6:
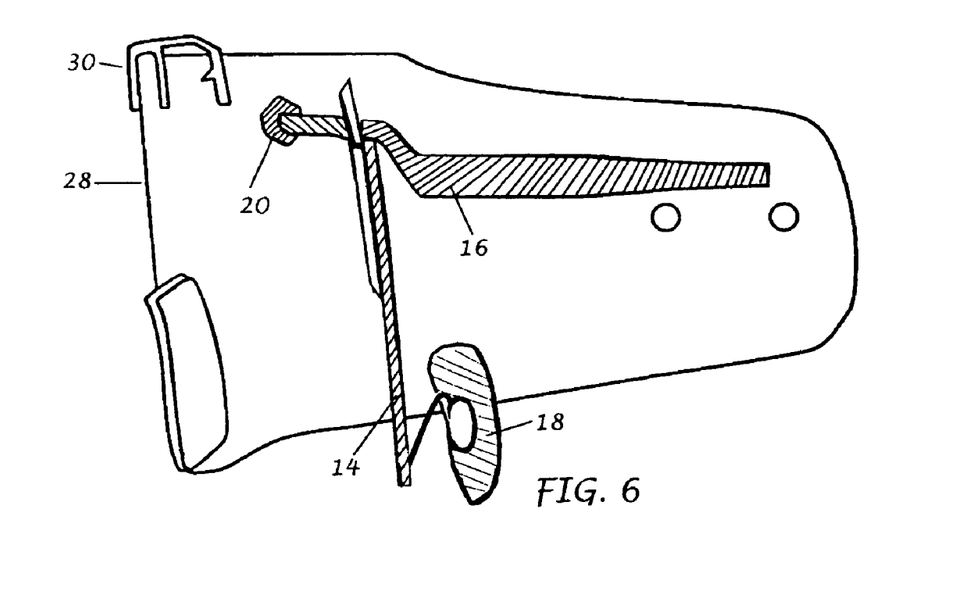
FIG. 6 is a cross-sectional view illustrating the primary safety eyewear of FIG. 1, being brought towards the primary eyewear of FIG. 3.
Figure 7:
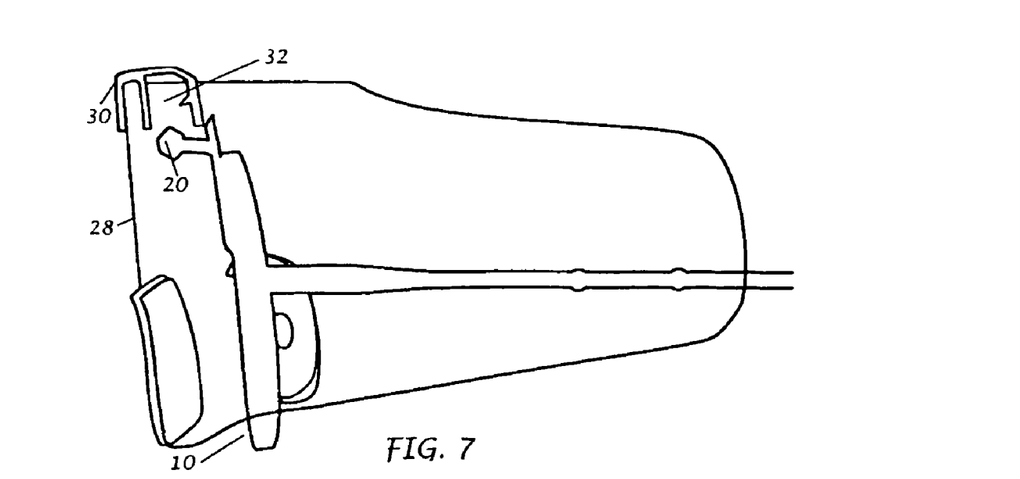
FIG. 7 is a cross-sectional view similar to FIG. 6, and illustrating a slot of the hinge member of the safety eyewear positioned above the hinge member of the primary eyewear.
Figure 8:
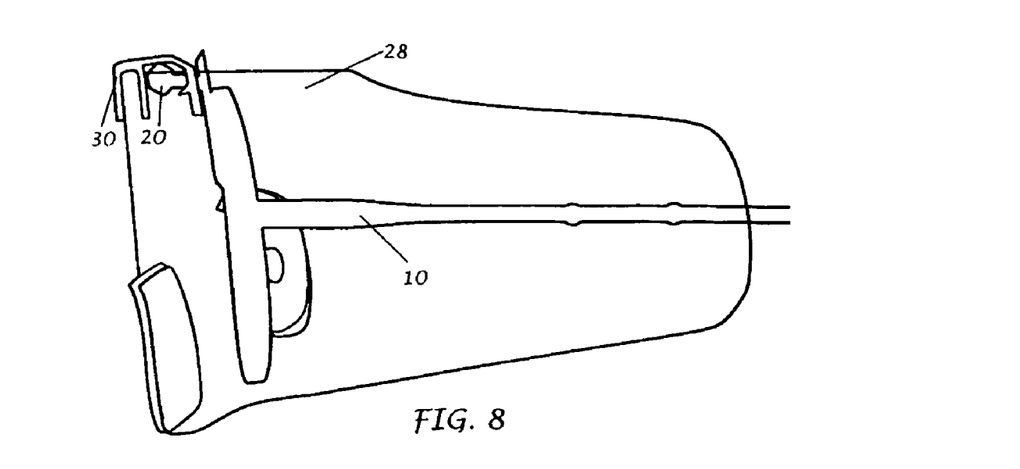
FIG. 8 is a cross-section view, similar to FIG. 7, illustrating the insertion of the primary eyewear hinge member into the slot of the hinge member of the safety eyewear.
Figure 9:
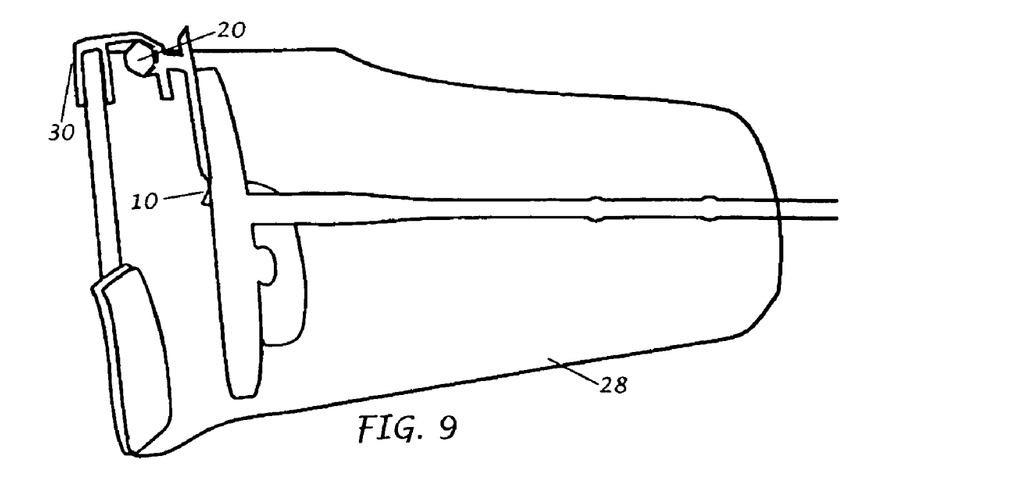
FIG. 9 is a cross-sectional view, illustrating magnetic coupling of the hinge members of the primary and secondary eyewear, in accordance with the present invention.
Figure 10:
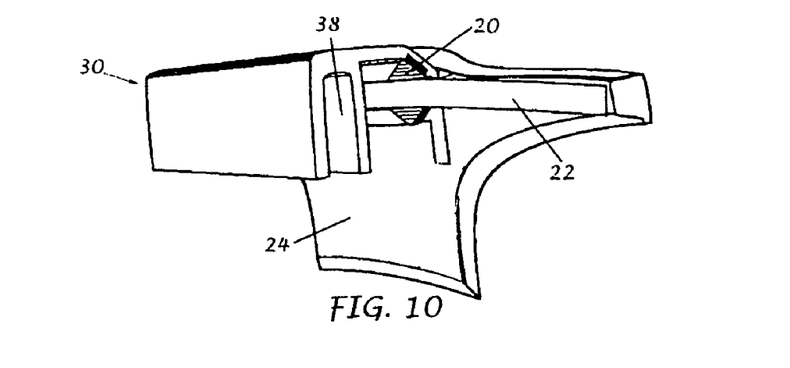
FIGS. 10 and 11 are enlarged perspective views, illustrating the coupling of the first and second hinge members, in accordance with the present invention.
Figure 11:
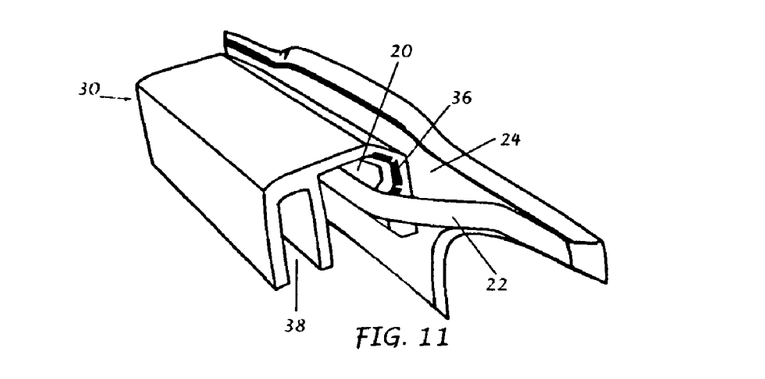

With reference to FIGS. 5–7, the primary eyewear 10 and the secondary eyewear 28 are removably coupled to one another by positioning auxiliary eyewear 28 generally parallel to the frontal plane of the primary eyewear 10, and moving the first slot 32 of the secondary hinge member 30 immediately over the first hinge member 20, as illustrated. As shown in FIGS. 8 and 9, the auxiliary eyewear 28 is then lowered until the first hinge member 20 of the primary eyewear 10 rests within the slot 32. The auxiliary eyewear 28 is then moved slightly forward, such that the magnetized facets 34 of the second hinge member 30 engage and magnetically couple with the rearward facets 26 of the primary hinge member 20. The facets 34 preferably engage the rearward facets 26 of the primary hinge member 20 so that if a projectile or the like contacts the auxiliary safety eyewear 28, although the magnetic coupling might become disengaged, the primary hinge member 20 will remain within the slot 32 and the auxiliary eyewear 28 remain in place and not become dislodged from the primary eyewear 10 or the head of the user.

Figure 12:
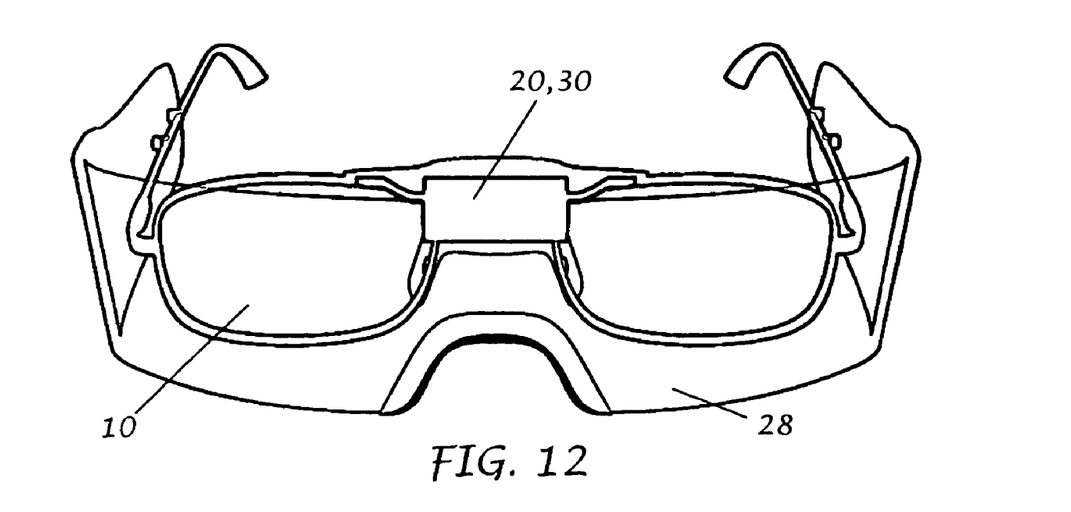
FIG. 12 is a front perspective view, illustrating the primary and auxiliary eyewear coupled to one another, in accordance with the present invention.
Figure 13:
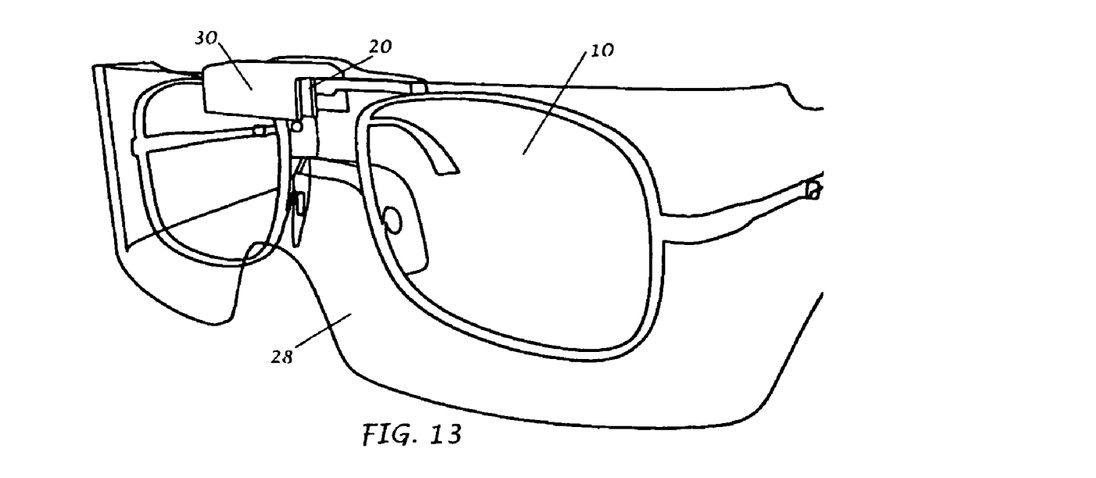
FIG. 13 is a side perspective view similar to FIG. 12, with the safety auxiliary eyewear in a closed or in-use position.
Figure 14:
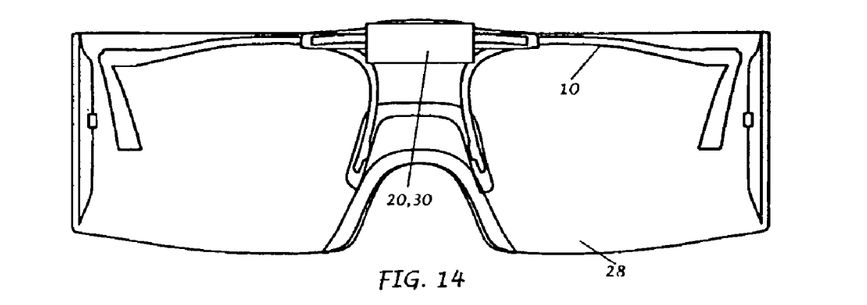
FIG. 14 is a front elevational view of the primary and secondary eyewear of FIGS. 12 and 13.
Figure 15:
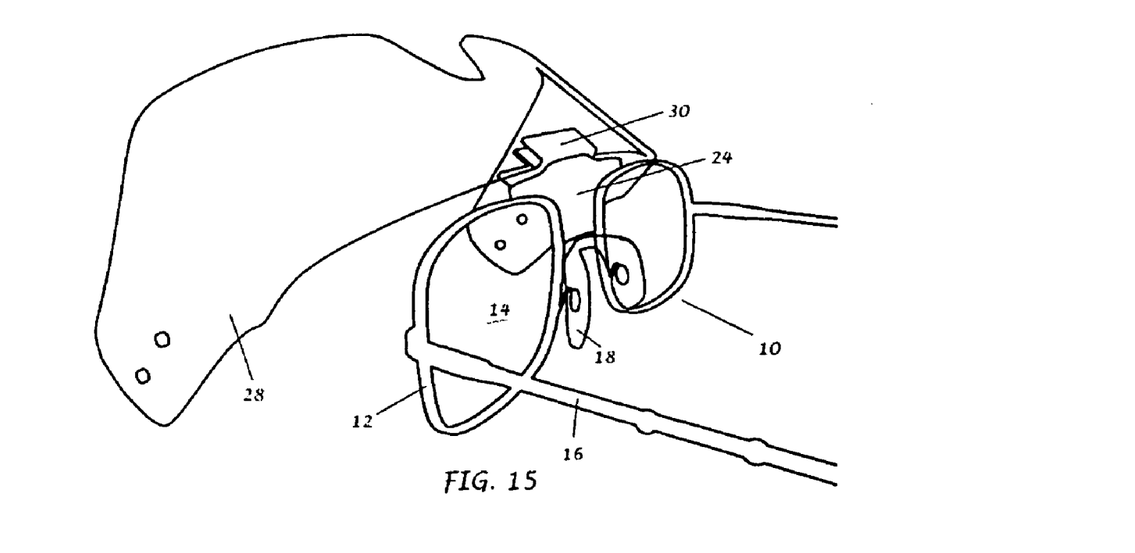
FIG. 15 is a side perspective view, illustrating the auxiliary safety eyewear pivoted upwardly into an open position relative to the primary eyewear.
Figure 16:
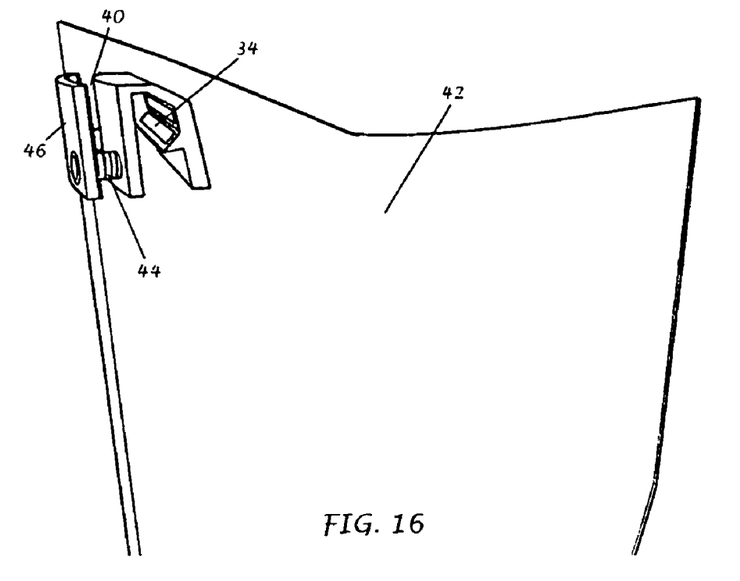
FIG. 16 is a side perspective view of another hinge assembly, attached to a safety face shield, in accordance with the present invention.
Figure 17:
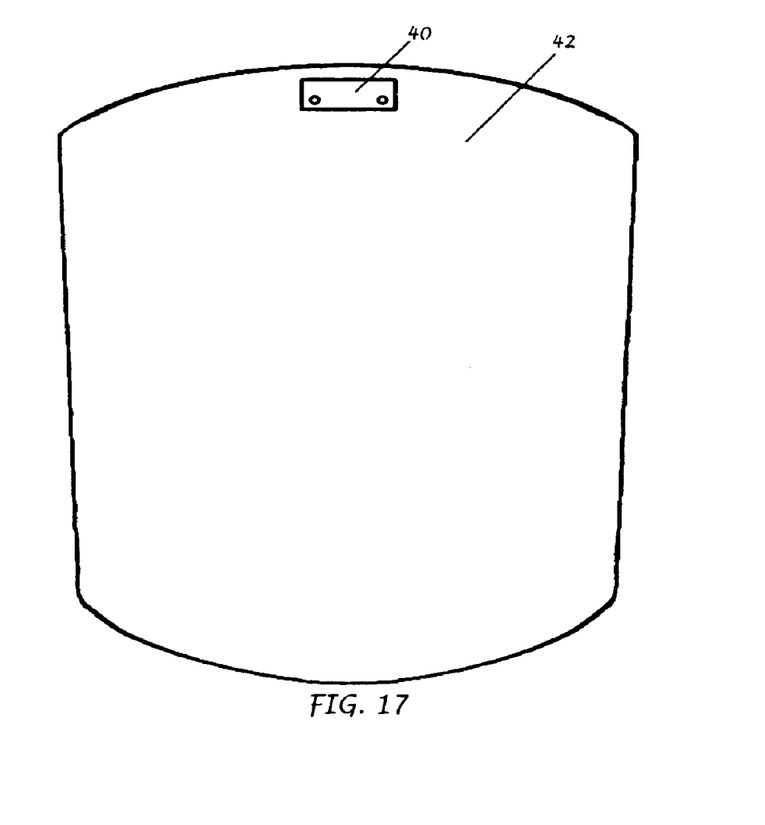
FIG. 17 is a front elevational view of a hinge member and safety shield of FIG. 16.
Figure 18:
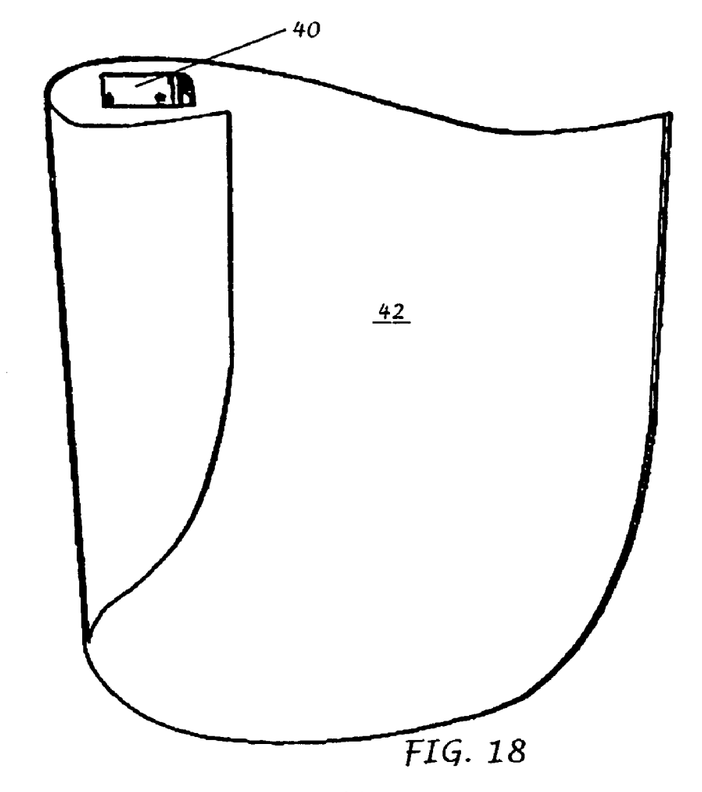
FIG. 18 is a rear perspective view of the face shield and hinge member of FIG. 16.
Figure 19:
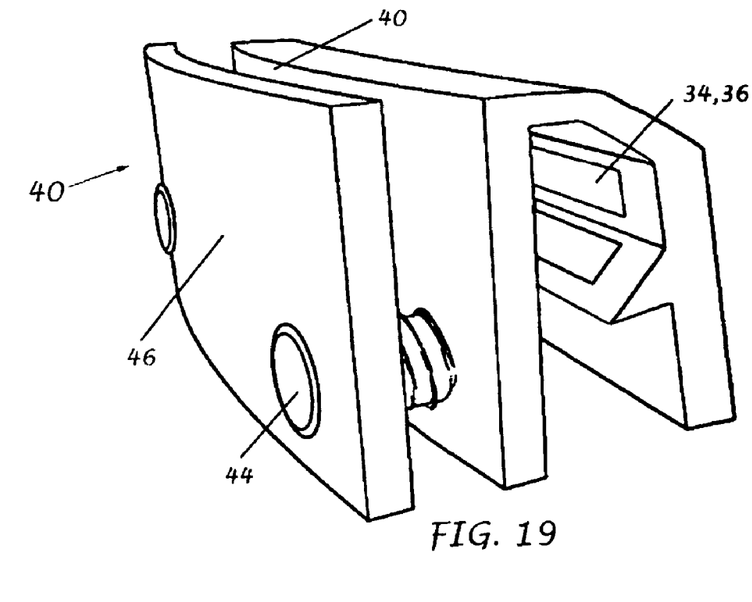
FIG. 19 is an enlarged perspective view of the hinge member of FIG. 16.

FIGS. 12–14 illustrate the auxiliary safety eyewear 28 coupled to the primary eyewear 10 by the engagement of the first and second hinge members 20 and 30, as described above. It will be appreciated that the magnets 36 or magnetic facets 34 create a magnetic field and attraction with the facets 26 of the hinge member 20. Due to the multi-faceted nature of the hinge members 20 and 30, and the fact that number of inwardly-facing facets 34 is less than that of the outwardly-facing facets 26, the hinge members 20 and 30 are capable of being selectively rotated in a segmented fashion. This is illustrated in FIG. 15, where the auxiliary safety eyewear 28 has been lifted upwardly into an open or out-of-view position with respect to the primary eyewear 10. When the auxiliary eyewear 28 is pulled upwardly, the facets 34 incrementally move from facet to facet 26 of the first hinge member 20, in this case 60° with each segment, until between 90° and 180° of rotation is achieved so that the auxiliary eyewear 28 is moved upwardly and out of the field of vision of the primary eyewear 10. Although the preferred embodiment, as illustrated, includes three inwardly-facing facets 34 which engage with three of the six outer facets 26 of the first hinge member 20, so as to overlie approximately 180° of the exterior surface of the first hinge member 20, it will be appreciated that the number of facets 26 and 34 can be varied to achieve the same objective. For example, the number of facets 26 and 34 can be decreased or increased in number and achieve the same objective.

With reference now to FIGS. 16–19, another embodiment of the present invention is illustrated wherein a second hinge member 40 is attached to a face shield 42. Similar to the previously described second hinge member 30, this hinge member also includes inwardly-facing facets 34 which are magnetized or include magnets embedded therein or attached thereto. However, in this case, a fastener 44 is used to secure the face mask 42 to the second hinge member 40. In particular, a screw fastener 44 extends between a second hinge member 40 and a plate 46 which cooperatively form a slot similar to slot 38 above, for retaining the face mask 42 therein. The second hinge member 40 is coupled to a first hinge member of a primary eyewear, as described above.

Figure 20:
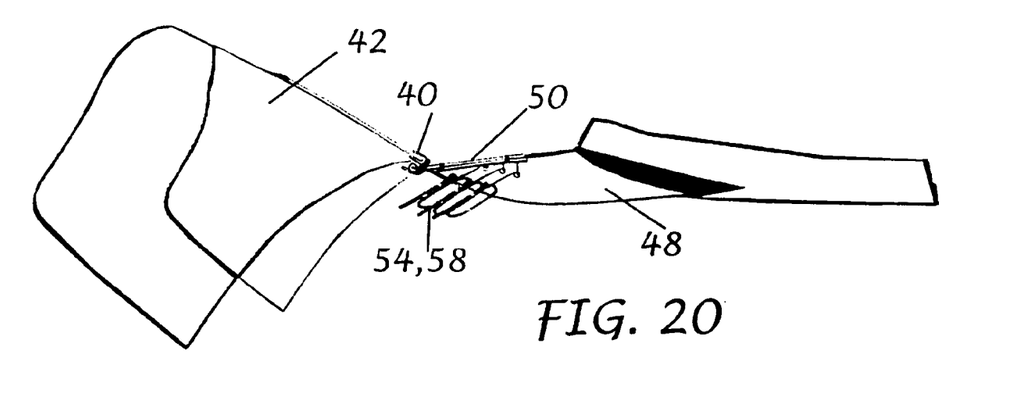
FIG. 20 is a side elevational view of a face safety shield, such as that illustrated in FIG. 16, and a series of eyewear attached to a track fastened to a bill of a visor, in accordance with the present invention.
Figure 21:
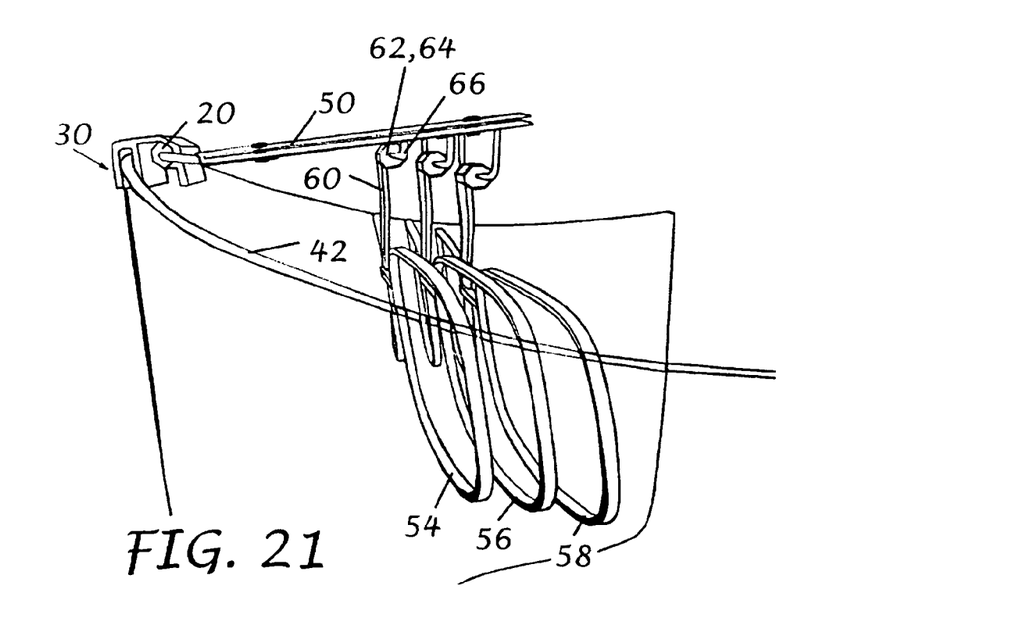
FIG. 21 is an enlarged perspective view of the track and face safety shield and eyewear extending therefrom, in accordance with the present invention.
Figure 22:
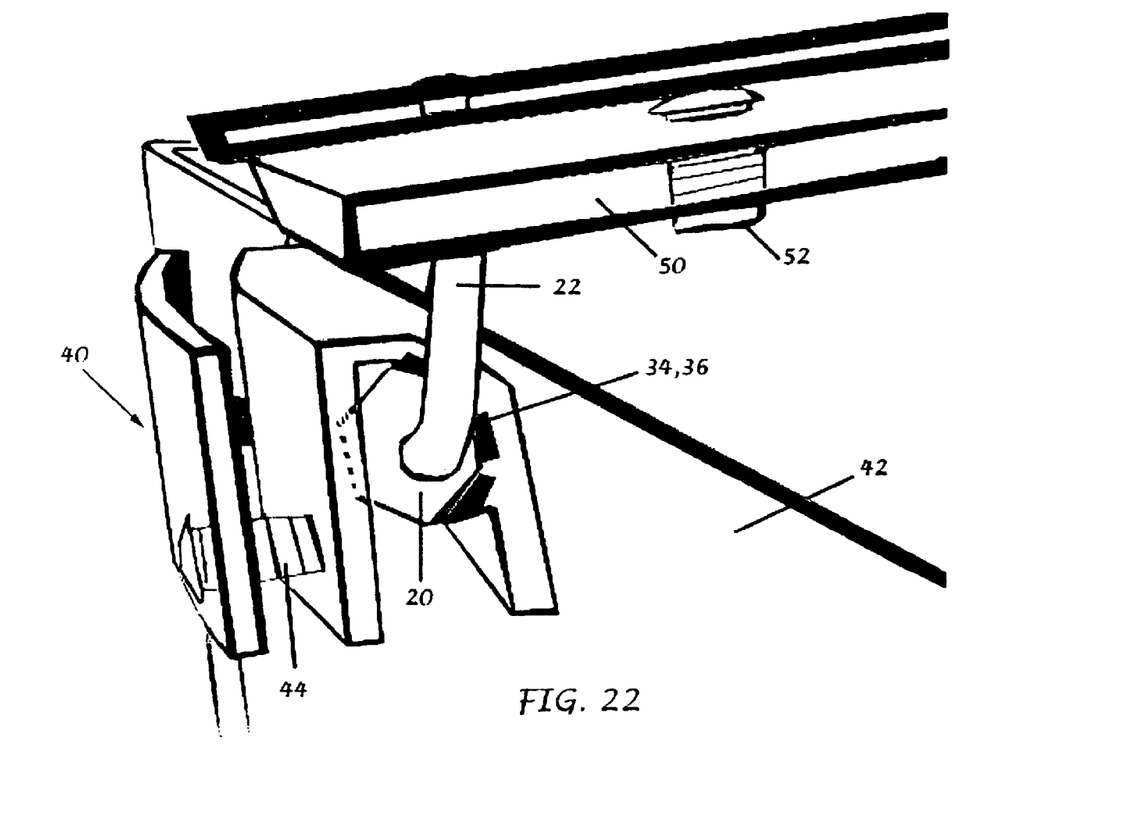
FIG. 22 is an enlarged perspective view of a hinge member attached to a safety shield, and magnetically coupled to a hinge member of the track, in accordance with the present invention.

With reference now to FIGS. 20–22, yet another embodiment of the present invention is illustrated. In this embodiment, the auxiliary safety eyewear, such as the illustrated face mask 42, is magnetically coupled to a bill 48 of a hat or visor by means of a track assembly 50. As shown in FIGS. 21 and 22, a second hinge member 30 or 40 is magnetically coupled to the first hinge member 20 which is connected to the tracks 50 by means of cross-bar 22 or the like in a manner similar to that described above, such that the auxiliary eyewear 42, in this case a face mask, is properly positioned in front of the eyes and face of the user. The pair of tracks 50 are secured to the bill 48 of the visor or hat by screws 52 or the like which extend through the tracks 50 and into the bill 48. In this manner, the tracks 50 and other reusable portions of the system can be attached to whichever hat or visor desired, even if the hat or visor is disposable, as might be the case in a surgery setting.

The auxiliary eyewear 42 is movable from before the face of the user, to an upward position, as illustrated in FIG. 20, and described above.

This particular embodiment is particularly useful for jewelers, surgeons, etc., where it might be desirable to have a plurality of auxiliary eyewear 54–58, etc. For example, in the case of a surgeon or jeweler, magnification may be needed. The auxiliary eyewear 54–58 each include an arm 60 having a third hinge member with a plurality of inwardly-facing facets which are magnetically attracted to and coupled with a hinge member 64 having a plurality of outwardly-facing facets and extending downwardly from the tracks 50, such as by means of cross-bars 66 or the like. The engagement of the facets of the hinge members 62 and 64 permit selective segmented rotation so as to increase or decrease the magnification by moving the auxiliary eyewear 54–58 into and out of alignment and view of the user. FIG. 21 illustrates all of the auxiliary eyewear 54–58 being generally parallel to the closed safety eyewear 42, so as to be viewed therethrough, also referred to as a panthoscopic angle. FIG. 20 illustrates all of the auxiliary eyewear 54–58 lifted upwardly so as to be out of the field of vision of the user. Of course, different combinations of the auxiliary eyewear 54–58 may be moved into the use position.

Although several embodiments have been described in detail for purposes of illustration, various modifications may be made to each without departing from the scope and spirit of the invention. Accordingly, the invention is not to be limited, except as by the appended claims.

What is claimed is:

1. A magnetic hinge system for rotatably and removably coupling a first object and a second object, comprising:
   a first hinge member associated with the first object, the first hinge member defining a hinge axis, and having a plurality of generally planar outwardly-facing facets disposed about the hinge axis; and
   a second hinge member attached to the second object and defining a slot having a plurality of generally planar inwardly-facing facets configured to overlie less than all of the outwardly-facing facets;
   wherein at least some of the facets of the second hinge member are magnetized or include magnets to couple the second hinge member to the first hinge member and permit selective segmented rotation of the second hinge member relative to the first hinge member about the hinge axis.

2. The system of claim 1, wherein the first hinge member includes at least five facets.

3. The system of claim 2, wherein the second hinge member includes at least half as many facets as the first hinge member.

4. The system of claim 3, wherein the first hinge member comprises a hexagon and the second hinge member includes three facets overlying three outwardly-facing facets of the hexagon simultaneously.

5. The system of claim 1, wherein approximately 180 degrees of the exterior surface of the first hinge member is overlied by the second hinge member.

6. The system of claim 1, wherein the first object comprises a primary eyewear, and the second object comprises a secondary eyewear.

7. The system of claim 6, including a crossbar attached to the primary eyewear frame and supporting the first hinge member.

8. The system of claim 7, wherein the crossbar is attached at opposite ends thereof to a plate attached to the primary eyewear frame, between a pair of lenses.

9. The system of claim 6, wherein the second hinge member defines a second slot configured for insertion of a portion of the secondary eyewear therein.

10. The system of claim 9, wherein the second slot includes a fastener for retaining the secondary eyewear therein.

11. The system of claim 6, wherein the facets of the second hinge member engage rear facets of the first hinge member when the primary and secondary eyewear are positioned parallel to one another.

12. The system of claim 6, wherein the secondary eyewear comprises safety eyewear.

13. A magnetic hinge system for rotatably and removably coupling primary and secondary safety eyewear, comprising:
   a crossbar associated with a frame of the primary eyewear, the crossbar supporting a first hinge member defining a hinge axis, and having at least five generally planar outwardly-facing facets disposed about the hinge axis; and
   a second hinge member attached to the secondary eyewear and defining a slot having a plurality of generally planar inwardly-facing facets numbering at least half as many facets as the first hinge member and configured to overlie approximately 180 degrees of the exterior surface of the first hinge member;
   wherein the facets of the second hinge member engage rear facets of the first hinge member when the primary and secondary eyewear are positioned parallel to one another; and
   wherein at least some of the facets of the second hinge member include magnets to couple the second hinge member to the first hinge member and permit selective segmented rotation of the second hinge member relative to the first hinge member about the hinge axis.

14. The system of claim 13, wherein the crossbar is attached at opposite ends thereof to a plate attached to the primary eyewear frame, between a pair of lenses.

15. The system of claim 13, wherein the first hinge member comprises a hexagon and the second hinge member includes three facets overlying three outwardly-facing facets of the hexagon simultaneously.

16. The system of claim 13, wherein the second hinge member defines a second slot configured for insertion of a portion of the second eyewear therein.

17. The system of claim 16, wherein the second slot includes a fastener for retaining the second eyewear therein.

18. A magnetic hinge system for eyewear, comprising:
   a track adapted for attachment to a first object and having a first hinge member associated therewith, the first hinge member defining a hinge axis, and having a plurality of generally planar outwardly-facing facets disposed about the hinge axis; and
   a second hinge member attached to a second object and defining a slot having a plurality of generally planar inwardly-facing facets configured to overlie less than all of the outwardly-facing facets of the first hinge member;
   wherein at least some of the facets are magnetized or include magnets to couple the second hinge member to the first hinge member and permit selective segmented rotation of the second hinge member relative to the first hinge member about the hinge axis.

19. The system of claim 18, wherein the track is attached to a bill of a hat or visor.

20. The system of claim 18, wherein the second hinge member is attached to an auxilliary eyewear.

21. The system of claim 20, wherein the auxilliary eyewear comprises a safety shield or eyewear.

22. The system of claim 20, wherein the second hinge member defines a second slot configured for insertion of a portion of the auxilliary eyewear therein.

23. The system of claim 22, wherein the second slot includes a fastener for retaining the secondary eyewear therein.

24. The system of claim 18, wherein the first hinge member includes at least five facets, and wherein the second hinge member includes at least half as many facets as the first hinge member so as to overlie approximately 180 degrees of the exterior surface of the first hinge member.

25. The system of claim 18, wherein the facets of the second hinge member engage rear facets of the first hinge when the primary and secondary eyewear are positioned parallel to one another.

26. The system of claim 18, including primary eyewear extending downwardly from the tracks.

27. The system of claim 26, including a third hinge member attached to the tracks and defining a hinge axis, and having a plurality of generally planar outwardly-facing facets disposed about the hinge axis, and a fourth hinge member attached to the primary eyewear and having a plurality of generally planar inwardly-facing facets configured to overlie less than all of the outwardly-facing facets of the third hinge member, wherein at least some of the facets are magnetized or include magnets to couple the third and fourth hinge members and permit selective segmented rotation of the fourth hinge member relative to the third hinge member.

* * * * *